(12) United States Patent
Nakamura et al.

(10) Patent No.: US 8,317,710 B2
(45) Date of Patent: Nov. 27, 2012

(54) BONE INSPECTING SYSTEM, AND LOWER LEG SUPPORTING DEVICE

(75) Inventors: Kozo Nakamura, Tokyo (JP); Isao Onishi, Tokyo (JP); Juntaro Matsuyama, Tokyo (JP); Kenji Tobita, Tokyo (JP); Ryoichi Sakai, Mitaka (JP); Koji Ogawa, Mitaka (JP); Koichi Miyasaka, Mitaka (JP); Eiichi Minagawa, Mitaka (JP)

(73) Assignees: The University of Tokyo, Tokyo (JP); Hitachi Aloka Medical, Ltd., Tokyo (JP)

( * ) Notice: Subject to any disclaimer, the term of this patent is extended or adjusted under 35 U.S.C. 154(b) by 93 days.

(21) Appl. No.: 13/055,405

(22) PCT Filed: Jul. 17, 2009

(86) PCT No.: PCT/JP2009/062989
§ 371 (c)(1),
(2), (4) Date: Jan. 21, 2011

(87) PCT Pub. No.: WO2010/010854
PCT Pub. Date: Jan. 28, 2010

(65) Prior Publication Data
US 2011/0130688 A1 Jun. 2, 2011

(30) Foreign Application Priority Data
Jul. 22, 2008 (JP) .................. 2008-188639

(51) Int. Cl.
*A61B 8/00* (2006.01)
*A61B 5/103* (2006.01)
*A61C 5/00* (2006.01)

(52) U.S. Cl. .................. 600/449; 600/439; 600/587

(58) Field of Classification Search ............ 600/437–44, 600/595, 587; 297/423.1–423.25, 16.1, 219.1, 297/330, 45, 284.11, 423.26, 68, 423.33; 5/29–39, 600, 618, 620, 611
See application file for complete search history.

(56) References Cited

U.S. PATENT DOCUMENTS 3,964,786 A * 6/1976 Mashuda ............... 297/330
(Continued)

FOREIGN PATENT DOCUMENTS
EP       2025291 A1    2/2009
(Continued)

OTHER PUBLICATIONS

International Search Report of PCT/JP2009/062989, mailing date Sep. 15, 2009.
(Continued)

*Primary Examiner* — Long V. Le
*Assistant Examiner* — Lawrence Laryea
(74) *Attorney, Agent, or Firm* — Westerman, Hattori, Daniels & Adrian, LLP

(57) ABSTRACT

Provided is a bone inspecting system for placing the lower legs (L) of an examinee (P) on a proximal support block (26) and a distal support block (28) mounted on a turning base (24). The proximal support block supports the heads of fibula, and the distal support block supports the lateral malleolus or medial malleolus of a tibial distal end of the examinee. The turning base is supported turnably on a turning axis positioned near the knees of the examinee, with respect to a main base (22), and is moved up and down by an elevating mechanism (30) disposed near the ankles. The turning base (24) is turned by the elevating mechanism while bearing the lower legs thereon, thereby positioning the lower legs horizontally.

7 Claims, 14 Drawing Sheets

U.S. PATENT DOCUMENTS

| | | | | |
|---|---|---|---|---|
| 4,700,373 | A | * | 10/1987 | Miller .......................... 378/177 |
| 7,806,823 | B2 | * | 10/2010 | Sakai et al. .................. 600/438 |
| 7,841,983 | B2 | | 11/2010 | Harada et al. |
| 2005/0004457 | A1 | * | 1/2005 | Moilanen et al. ............. 600/437 |
| 2005/0085728 | A1 | * | 4/2005 | Fukuda ......................... 600/449 |
| 2006/0241447 | A1 | | 10/2006 | Harada et al. |
| 2008/0242970 | A1 | | 10/2008 | Minagawa et al. |
| 2010/0185086 | A1 | * | 7/2010 | Suetoshi et al. .............. 600/438 |

FOREIGN PATENT DOCUMENTS

| | | |
|---|---|---|
| JP | 10-052459 A | 2/1998 |
| JP | 2000-175911 A | 6/2000 |
| JP | 2002-065386 A | 3/2002 |
| JP | 2002-085463 A | 3/2002 |
| JP | 2002-330965 A | 11/2002 |
| JP | 2006-280532 A | 10/2006 |
| JP | 2007-301284 A | 11/2007 |
| JP | 2008-245738 A | 10/2008 |

OTHER PUBLICATIONS

Japanese Office Action dated Sep. 29, 2009, issued in corresponding Japanese Patent Application No. 2008-188639.

Notification of Transmittal of Translation of the International Preliminary Report on Patentability (Form PCT/IB/338) of International Application No. PCT/JP2009/062989 mailed Mar. 17, 2011 with Form PCT/IPEA/409.

* cited by examiner

BONE INSPECTING SYSTEM, AND LOWER LEG SUPPORTING DEVICE

TECHNICAL FIELD

The present invention relates to a bone inspection system directed to examining the lower leg, and particularly to a technique of positioning a portion to be examined when inspecting a bone using ultrasound.

BACKGROUND ART

There has been proposed a system for evaluating the property of a bone based on a minute displacement caused when a load is applied to the bone. Patent Literature 1 indicated below discloses a system directed to measuring a tibia in a lower leg of a living body. A load is applied to the tibia from outside the body via the skin, and deformation of the tibia caused by the load is measured using ultrasound. Based on the measured deformation, physical indices indicating characteristics such as resilience, viscoelasticity, and plasticity of the tibia are determined. These physical indices are recognized to indicate the property, soundness, coaptation, and the like of the tibia.

CITATION LIST

Patent Literature

Patent Literature 1: JP 2007-301284 A

SUMMARY OF THE INVENTION

Technical Problems

As the object of measurement is bone, its displacement is very minute. Accordingly, it is necessary to position the measurement object portion in an appropriate orientation. Further, in order to minimize the burden on the examined person, it is desired that the positioning can be performed easily.

An object of the present invention is to enable easy positioning of a measurement object portion, particularly the lower leg.

Solution to the Problems

According to one aspect of the present invention, there is provided a bone inspection system including a lower leg support device for supporting a lower leg of an examined person, a load applying mechanism for applying a load to a bone of the supported lower leg, and an ultrasonic unit that transmits and receives ultrasonic waves to and from the lower leg bone and carries out a measurement based on a received ultrasonic signal, wherein a deformation in the bone caused by the load is measured using the ultrasonic unit. The lower leg support device includes a main base, a pivoting base that is pivotably supported with respect to the main base, and a proximal support member and a distal support member that are provided commonly on the pivoting base and individually support a proximal portion and a distal portion of the lower leg, respectively. The axis of pivot of the pivoting base is located in a position corresponding to the proximal portion of the lower leg, and the pivoting action causes the distal portion to be raised and lowered.

By arranging the proximal support member and the distal support member commonly on the pivoting base, positioning of the lower leg can be achieved by the pivoting action of the pivoting base. The axis of pivot is located at a position corresponding to the proximal portion of the lower leg, such that the pivoting action causes the distal portion to be raised and lowered. The lower leg is positioned such that its orientation along the lengthwise direction becomes orthogonal to the direction along which the load is applied. Typically, the load application direction is vertical, and the lower leg is positioned horizontally. In a case where the proximal support member and the distal support member are adjusted independently of each other, positional adjustment of one portion of the lower leg may result in a change in the position of the other portion, making it difficult to achieve proper adjustment. According to the present invention, by configuring to adjust the lengthwise orientation of the lower leg by the pivoting action of the pivoting base, only a single adjustment element is provided, thereby facilitating adjustment. Furthermore, the axis of pivot is located at a position corresponding to the proximal portion of the lower leg. This arrangement is provided considering the fact that because the proximal end of the lower leg, namely the knee, is connected to the upper leg and further to the torso, the proximal portion of the lower leg is less easily moved compared to the distal portion.

The distal support member is configured such that its mounting position on the pivoting base is changeable, so that adaptations can be made in accordance with individual differences, typically body size differences, of the examined persons. Because the range of movement of the proximal portion of the lower leg is limited as explained above, in a simplified configuration, the position on the pivoting base may be changeable only for the distal support member. However, in order to permit a large range of adjustment, it is desirable to configure such that the position of the proximal support member on the pivoting base is also changeable.

Two lower leg support sets, each including the pivoting base, the proximal support member, and the distal support member, may be provided, so that both left and right lower legs can be supported simultaneously. According to this arrangement, examination can be performed successively for the two lower legs, thereby improving efficiency of examination. Further, even when the actual object of measurement is one of the legs, there may be cases in which the other leg is measured as an object of comparison. For such cases too, it is preferable to provide two lower leg support sets.

The above-mentioned load applying mechanism may be swingably supported on a column. The column is provided between the two lower leg support sets. By swinging the load applying mechanism, load can be applied to an object located on either of the left and the right. By the swinging operation, the point of load application can be easily switched from left to right and right to left.

The above-mentioned column may be configured to support an ultrasonic probe that constitutes a part of the ultrasonic unit and transmits and receives ultrasonic waves. By swingably supporting the ultrasonic probe together with the load applying mechanism, the load applying mechanism and the ultrasonic probe can easily switch between objects of examination located on the left and the right.

The load applying mechanism includes a rocking lever and a weight that performs a reciprocating linear movement along this lever. By the reciprocating linear movement of the weight, the load applying mechanism is able to apply load that varies periodically.

Advantages of the Invention

According to the present invention, the lower leg can be easily and appropriately positioned. Further, the burden on the examined person can be minimized.

EMBODIMENTS OF THE INVENTION

An embodiment of the present invention is next explained referring to the drawings. FIG. 1 shows a schematic configuration of a bone inspection system 10 according to the present embodiment. An examined person P is seated on a chair 12, and his lower leg L is placed on a lower leg support device 14. A load applying mechanism 16 is arranged facing the lower leg L of the examined person. Further, on both sides of the point of load application to the lower leg L by the load applying mechanism, ultrasonic probes 20 of an ultrasonic diagnosis apparatus 18 are provided. The lower leg support device 14 includes a main base 22 placed on the floor, and a pivoting base 24 pivotably supported on the main base 22. The pivoting base 24 has a shape of an elongate plate extending substantially parallel to the lower leg L. Mounted on the upper surface of the pivoting base 24 are a proximal support block 26 that supports the lower leg at a predetermined proximal position, and a distal support block 28 that supports the lower leg at a predetermined distal position. These support blocks 26, 28 can be mounted on the pivoting base 24 at arbitrary positions so that adaptations can be made in accordance with individual differences of the examined persons P. The axis of pivot of the pivoting base 24 extends in a direction along the left and right direction of the examined person P, and is located toward the proximal portion of the lower leg. In the main base 22, at a position corresponding to the distal end of the pivoting base 24, an elevating mechanism 30 is provided. By using this mechanism 30 to raise or lower the distal end of the pivoting base, the pivoting base 24 is pivoted. The ankle side or the distal portion of the lower leg L is raised and lowered with respect to the knee side or the proximal portion by the pivoting action of the pivoting base 24.

By supporting the lower leg L at the proximal portion and the distal portion and applying a load at a central portion of the lower leg, a bending load is made to act on the lower leg. The bone inspection system 10 serves to measure a deflection in a bone (which may be the tibia) caused by this bending load acting on the lower leg. When the tibia is the object of measurement, the preferable points for supporting the lower leg are the head of the fibula on the proximal side and the lateral malleolus or medial malleolus of the tibia on the distal side. These portions are preferred as measurement reference points because, at these portions, the position of the bone can be easily identified visually or by touch from outside via the thin skin. A preferable position for the load application point is a location on the medial surface on the front side of the tibia, where the medial bone surface of the shin is planar. This portion of the tibia is located immediately below the skin and forms a planar surface extending in the axis direction. It is preferable to position the lower leg such that this planar surface is oriented substantially horizontally. By applying a load at the load application point and measuring a resulting displacement using the ultrasonic diagnosis apparatus 18, physical indices indicating characteristics such as resilience of the bone to be examined can be obtained.

In the following explanation, the terms "longitudinal", "transverse", and "vertical" denote the directions from the perspective of the examined person P seated in the posture shown in FIG. 1. More specifically, the left and the right for the examined person P are referred to below as the transverse or left and right direction, and the vertical direction for the examined person P is referred to as the vertical or up and down direction. Further, the direction along which the lower legs of the examined person P extend and which is orthogonal to the transverse and vertical directions is referred to below as the longitudinal or front and rear direction.

FIGS. 2 and 3 are perspective views showing the lower leg support device 14. FIG. 3 shows a view from the opposite side of the view shown in FIG. 2, and additionally illustrates the lower legs in the supported state in dot-and-dash lines. The main base 22 includes a top plate 32 having a substantially rectangular shape and supported by four legs. In the top plate 32 at the central portion along the widthwise direction, there is formed a top plate slit 34 extending in the lengthwise direction. On both sides of the top plate slit 34, pivoting bases 24 are positioned parallel to the slit 34. The pivoting bases 24 are pivotably supported on a support axis 36 at a position corresponding to the proximal portion of the placed lower legs. On each pivoting base 24, a proximal support block 26 and a distal support block 28 are arranged. On the lower side of the top plate 32, an elevating mechanism 30 for raising and lowering the distal end of the pivoting base 24 is provided for each of the two pivoting bases 24 located on the left and the right. Accordingly, the left and right pivoting bases 24 can be adjusted separately of each other.

A column 38 is arranged standing up through the top plate slit 34. A device for supporting the column 38 is provided below the top plate 32, but this device is not shown in FIGS. 2 and 3. An explanation of this device is given later. At the top of the column 38, there are provided a load applying mechanism 16 and probe retaining arms 40 for retaining ultrasonic probes 20. As shown in the figures, in the lower leg support device 14 according to the present embodiment, each of the two ultrasonic probes 20 is supported by one probe retaining arm, such that the positions of the two ultrasonic probes 20 can be adjusted independently of each other. The load applying mechanism 16 includes a rocking lever 42 and a weight 44 that is moved on and along this rocking lever 42. A pressing element 126 (see FIGS. 12 and 13) that contacts and applies a load to the lower leg is further provided at the tip portion of the rocking lever 42. By moving the weight 44, predetermined loads can be applied. The rocking lever 42 is mounted on a transverse adjustment guide 46. By moving the rocking lever 42 along this guide, the position of the load application point along the transverse direction with respect to the examined person can be adjusted. A detailed explanation of the load applying mechanism 16 is given later.

The upper portion of the column 38 can be swiveled about the axis of the column. As a result of this swiveling, the components mounted on the upper portion of the column 38, such as the load applying mechanism 16 and the probe retaining arms 40, are swung around. By means of this swinging, the object of measurement can be easily changed from the right lower leg to the left lower leg, and vice versa. The column 38 is supported below the top plate 32 in a vertically displaceable manner, and also movable in the direction along the top plate slit 43. The structure supporting the column 38 is described later.

FIGS. 4-7 show the structure of the lower leg support set including the pivoting base 24 and the proximal and distal support blocks 26, 28. FIG. 4 is a perspective view, FIG. 5 is a side view, FIG. 6 is a cross-sectional view taken along line A-A shown in FIG. 5, and FIG. 7 is a front view. A bearing holder 48 is fixed to the top plate 32 of the main base, and the support axis 36 is supported therein. The pivoting base 24 is also provided with a bearing holder 50, by which the pivoting base 24 is pivotably supported on the support axis 36. The proximal support block 26 includes a magnet base 52 and a receiving member 54. By means of the magnet base 52, the proximal support block 26 can be positioned in place at an arbitrary position on the plate-shaped pivoting base 24. In order to enable adhesion of the magnet base 52, the pivoting base 24 is composed of a ferromagnetic material, which is typically steel. The entire pivoting base 24 need not be formed with steel, and the pivoting base 29 may be formed by attaching a steel plate on its upper surface only, where the magnet base 52 is to be placed. The main material constituting the receiving member 54 is a material having sufficient rigidity, which may for example be a light metal such as aluminum or a hard resin. Meanwhile, in order to provide a soft touch, a soft pad made of silicone rubber or the like may be attached to the surface of the receiving member 54. The receiving member 54 has a shape of a plate curved in the form of an arc segment, and this arc segment ranges over the angle of approximately 90° when viewed from the center of the arc, with the radius of curvature being 90 mm. This arc segment angle is determined for enabling the proximal support block 26 to support the head of the fibula located at the proximal portion of the lower leg and to position the planar portion of the medial side surface of the tibia in a horizontal manner as explained above.

The distal support block 28 has an almost identical structure to the proximal support block 26. That is, the distal support block 28 is formed by providing a receiving member 58 having a shape of a curved plate on a magnet base 56. The distal support block 28 can similarly be positioned in place using the magnet base 56 at an arbitrary position on the pivoting base 24. Although the receiving member 58 is has the same arc segment shape as the proximal receiving member 54, the radius of curvature of the receiving member 58 is 60 mm and therefore slightly smaller. This difference is based on fact that the proximal end and distal end of a human lower leg have different sizes. Further, the portion of the receiving member 58 corresponding to the outward side of the lower leg when viewed from the front is formed to extend longer. More specifically, the arc segment of the inward portion ranges over the angle of 40° when viewed from the arc center, while the arc segment of the outward portion ranges over the angle of 60°. This arrangement is provided so that that the lateral malleolus located at the distal end of the tibia abuts the receiving portion 58. As can be seen in FIG. 7, the distal receiving portion 58 is arranged at a somewhat higher position (in this embodiment, 30 mm) compared to the position of the proximal receiving portion 54. This difference is also provided based on fact that the distal end of a lower leg has a smaller size.

FIG. 8 shows the elevating mechanism 30 that raises and lowers the distal end of the pivoting base 24 to thereby cause the pivoting base 24 to be pivoted about the support axis 36. FIG. 8 is a cross-sectional view of a side opposite from the side appearing in FIG. 2. An elevating mechanism housing 60 has two guide rods 62 extending parallel to each other along the vertical direction. Linear bushings 64 are respectively guided on the guide rods 62. The two linear bushings 64 are coupled to a common rod holder 66. The rod holder 66 is protruded upward and retains a pushup rod 68 that abuts the lower surface of the pivoting base 24. A feed screw shaft 70 is arranged parallel to the guide rods 62, and a feed screw nut 72 that engages the feed screw shaft 70 is fixed to the rod holder 66. A worm wheel 74 is integrally provided on the feed screw shaft 70, and the worm wheel 74 engages a worm 78 coupled to a handle 76. By rotating the handle 76, the feed screw shaft 70 is rotated via the worm 78 and the worm wheel 74. As a result, the rod holder 66 and the pushup rod 68 which constitute a single unit are raised and lowered.

FIGS. 9-11 show the column 38 and the mechanism that supports and displaces the column 38 in horizontal and vertical directions. FIG. 9 is a perspective view from above the top plate 32, FIG. 10 is a perspective view from the underside of the top plate 32, and FIG. 11 is a cross-sectional view showing the support structure of the column 38.

As shown in FIG. 10, on the lower surface of the top plate 32, linear guide rails 80 are provided on both sides of the top plate slit 34 and parallel to the slit 34. Slide blocks 82 that move along these linear guide rails 80 are engaged on those rails 80. For the purpose of simplification only, the cross-sectional shapes of the rails and the grooves in the blocks are illustrated in the figure as being rectangular. However, in actual practice, the cross-sections have dovetail joint shapes so that the blocks do not fall off in the direction orthogonal to the rails. By being suspended by the slide blocks 82, a column support mechanism 84 is arranged below the top plate 32. The column support mechanism 84 slides along the linear guide rails 80, thereby causing the column 38 to slide along the top plate slit 34.

The column support mechanism 84 includes a moving base 86 that moves along the linear guide rails 80, and a vertical displacement base 88 that is additionally vertically displaced relative to the moving base. The moving base 86 is provided with linear guide rails 90 extending in the vertical direction. A slide block 92 that engages these rails 90 is fixed to the vertical displacement base 88. The cross-sections of these linear guide rails 90 and the slide block 92 also have dovetail joint shapes, such that while the block 92 is allowed to move in the direction along the rails 90, the block 92 is not removable in the direction orthogonal thereto. A tensile force provided by a constant load spring 94 is made to act on the vertical displacement base 88 to thereby cancel at least a part of the weight of the vertical displacement base 88 itself, the column 38, and the load applying mechanism and the like mounted at the top of the column. The vertical displacement base 88 is provided with a crossed roller bearing 98 and a crossed roller bearing holder 100 that retains the bearing 98. The outer race 102 of the crossed roller bearing 98 is fixed to the vertical displacement base 88, and the column 38 is fixed to the inner race 104. According to this arrangement, the column 38 can be swiveled about its axis relative to the vertical displacement base 88.

A feed screw bracket 108 to which a feed screw nut 106 is fixed is provided in the vicinity of the lower end of the moving base 86. A feed screw shaft 110 is screwed and coupled to the feed screw nut 106. The feed screw shaft 110 extends upward, penetrates through the inside of the crossed roller bearing 98 and the column 38, and reaches the upper portion of the column 38. An adjustment disc 112 is arranged at the upper portion of the column 38 (refer to FIG. 9), and the upper end of the feed screw shaft 110 is fixed to this adjustment disc 112. The adjustment disc 112 is partially exposed outside from slits formed in the four sides of a column top box 114. By touching the exposed portion with a finger and rotating the adjustment disc 112, the feed screw shaft 110 is also rotated together with the adjustment disc 112. When the feed screw shaft 110 is rotated, the screw shaft 110 itself is displaced upward and downward. Along with the upward and downward displacement of the screw shaft 110, the column 38 and the vertical displacement base 88 are displaced vertically.

FIGS. 12-14 show the structure of the load applying mechanism 16. FIG. 12 is a perspective view, FIG. 13 is a lengthwise cross-sectional view, and FIG. 14 is a cross-sectional view taken along line B-B shown in FIG. 13. The transverse adjustment guide 46 is fixed to the top of the column 38. The transverse adjustment guide 46 is provided with two linear guide rails 116 extending along the left and right direction and facing each other. Further, slide blocks 118 are respectively engaged on these linear guide rails 116. The slide blocks 118 are fixed to a rocking axle holder 122 that supports a rocking axle 120. According to this arrangement, the rocking axle holder 122 slides in the transverse direction along the linear guide rails 116 together with the rocking axle 120. Further, the rocking axle holder 122 is provided with a locking screw 124 for stopping this sliding rocking axle. By rotating the screw 124 to cause this screw to abut the transverse adjustment guide 46, the rocking axle holder 122 becomes fixed and its position along the transverse direction becomes determined. The transverse adjustment guide 46 is further provided with two arm holders 125 for holding the probe retaining arms 40.

The rocking lever 42 is pivotably supported on the rocking axle 120, and is moved in the transverse direction together with the sliding of the rocking axle holder 122. At the lower portion of the tip of the rocking lever 42, there is provided a pressing element 126 which is the element that contacts the examined person's tibia via the skin. The pressing element 126 includes a load cell 128 that measures a load applied to the tibia. By adjusting the position of the rocking axle holder 122 along the transverse direction, the pressing element 126 is positioned to contact the lower leg at a predetermined position.

A weight 44 slides on a linear guide rail 130 provided on the rocking lever 42. Further, inside the rocking lever 42, a feed screw shaft 132 is provided extending along the lengthwise direction of the rocking lever 42. A feed screw nut 134 that screws and couples to this feed screw shaft 132 is fixed to the weight 44. A drive motor 136 is coupled to the feed screw shaft 132, and the drive motor 136 drives the feed screw shaft 132 to thereby cause the weight 94 to slide. By this sliding of the weight 44, a change is caused in the moment generated by the weight around the rocking axle 120, such that the load applied by the pressing element 126 is changed. By changing the load periodically and measuring the deformation caused in the tibia in response, the bone physical characteristics are evaluated.

A flow of the inspection procedure is next explained. The examined person P is seated on the chair 12, and one or both of the lower legs are placed on the proximal and distal support blocks 26, 28 located on the pivoting base 24. The foot (the part located toward the distal direction from the ankle) is turned slightly outward so that the head of fibula and the lateral malleolus at the distal end of tibia are abutted against the support blocks 26, 28, respectively. Subsequently, the elevating mechanism 30 is operated, specifically by rotating the handle 76, so as to raise or lower the distal end of the pivoting base 24. The axis of pivot of the pivoting base 24 is located near the proximal portion of the lower leg, so that the parts that are supporting the lower leg are substantially unmoved. By the turning of the foot and the pivoting of the pivoting base 24 caused by the elevating mechanism 30, an adjustment is made such that the medial planar surface of the tibia is oriented horizontally.

Next, the position of the column 38 in the longitudinal direction (the direction along which the lower leg extends) is adjusted in order to position the column 38 so that a load can be applied to the tibia at a predetermined location along its axis. This adjustment is carried out by holding, pushing, and moving the column 38 or the load applying mechanism or the like mounted on the column. Further, height adjustment and transverse adjustment are carried out. The height adjustment is performed by rotating the adjustment disc 112, so as to position the rocking lever 42 horizontally. The transverse adjustment is performed by moving the rocking axle holder 122 relative to the transverse adjustment guide 46. By performing these steps, adjustment is achieved such that the pressing element 126 contacts the tibia.

The ultrasonic probes 20 are applied at both sides of the position of the pressing element 126 along the tibia extending direction. The drive motor 136 is driven to cause the weight 44 to perform a reciprocating movement along the axis of the rocking lever 42, thereby applying load that varies periodically. The displacement of the tibia in response to the application of load is measured using the ultrasonic diagnosis apparatus 18.

When measurement of the other lower leg is to be performed, the column 38 is rotated so that the load applying mechanism 16 and the like are swung around. The rotation of the column is achieved by means of the crossed roller bearing 98. Both the left and right legs are measured not only when bones in both legs are broken and the both legs need to be examined, but also in cases where the healthy one of the legs is used as a reference for evaluating a bone in the other leg which is the object of examination. In such cases too, the present embodiment can facilitate and speed up the procedure.

Figure 1:
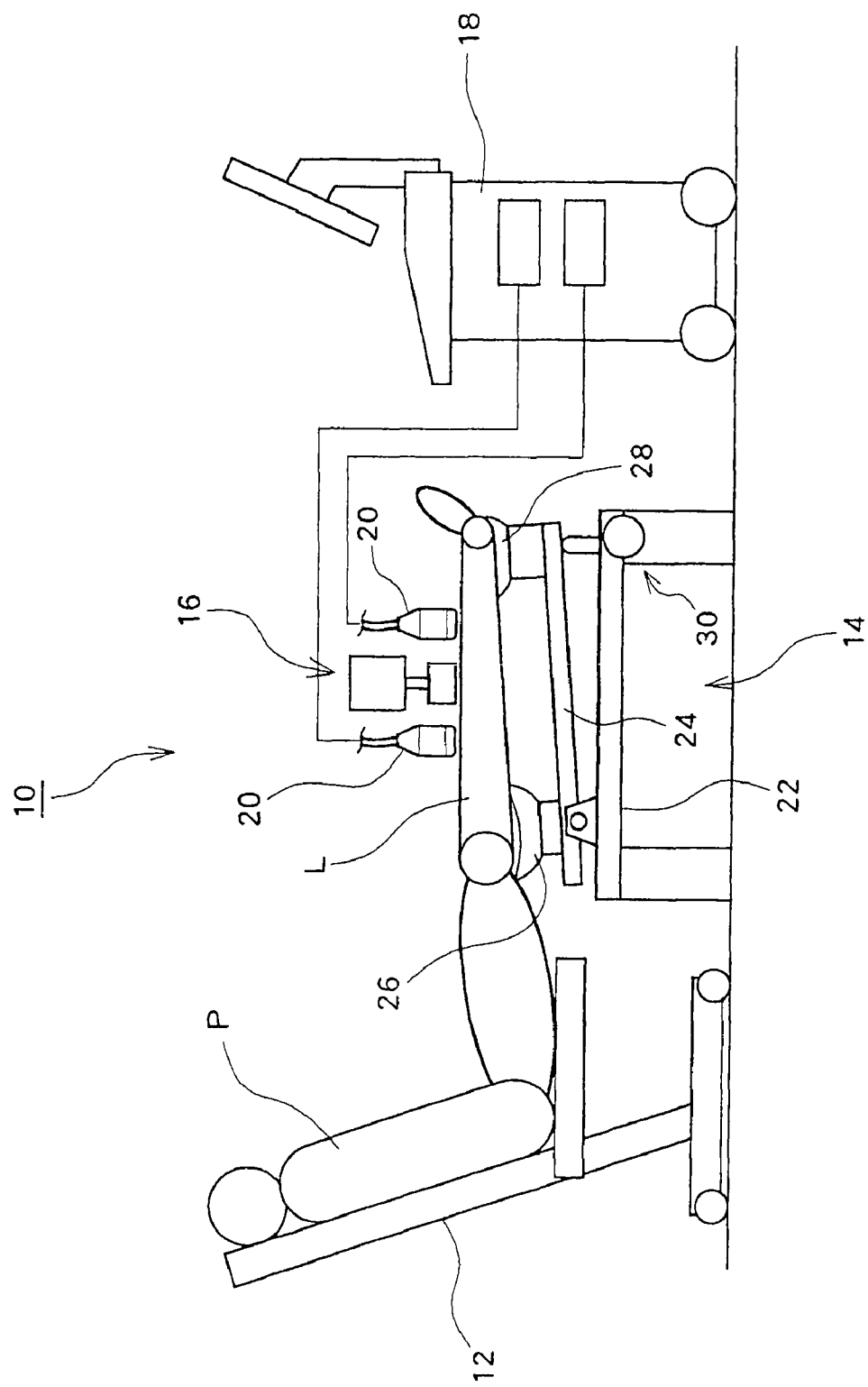
FIG. 1 is a schematic configuration diagram showing a bone inspection system.
Figure 2:
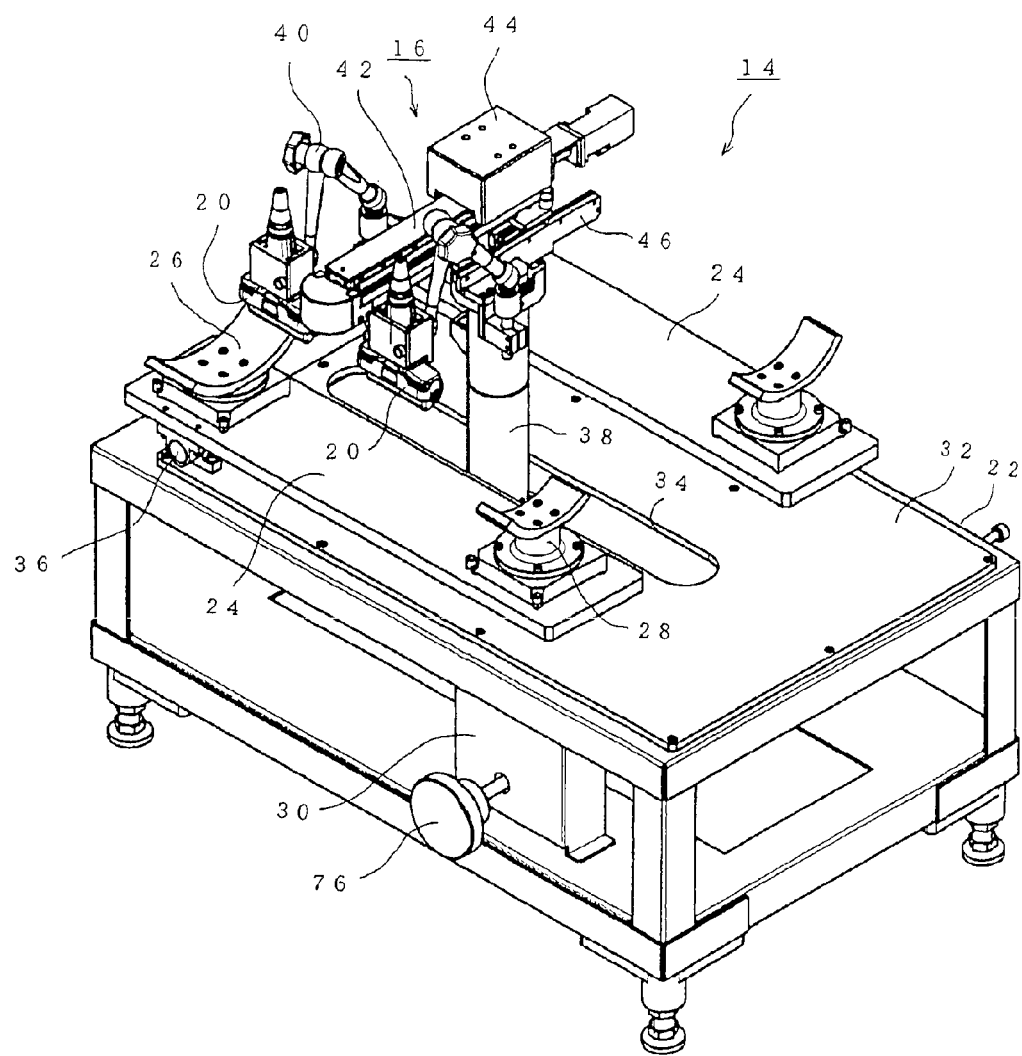
FIG. 2 is a perspective view showing a lower leg support device 14 according to the present embodiment.
Figure 3:
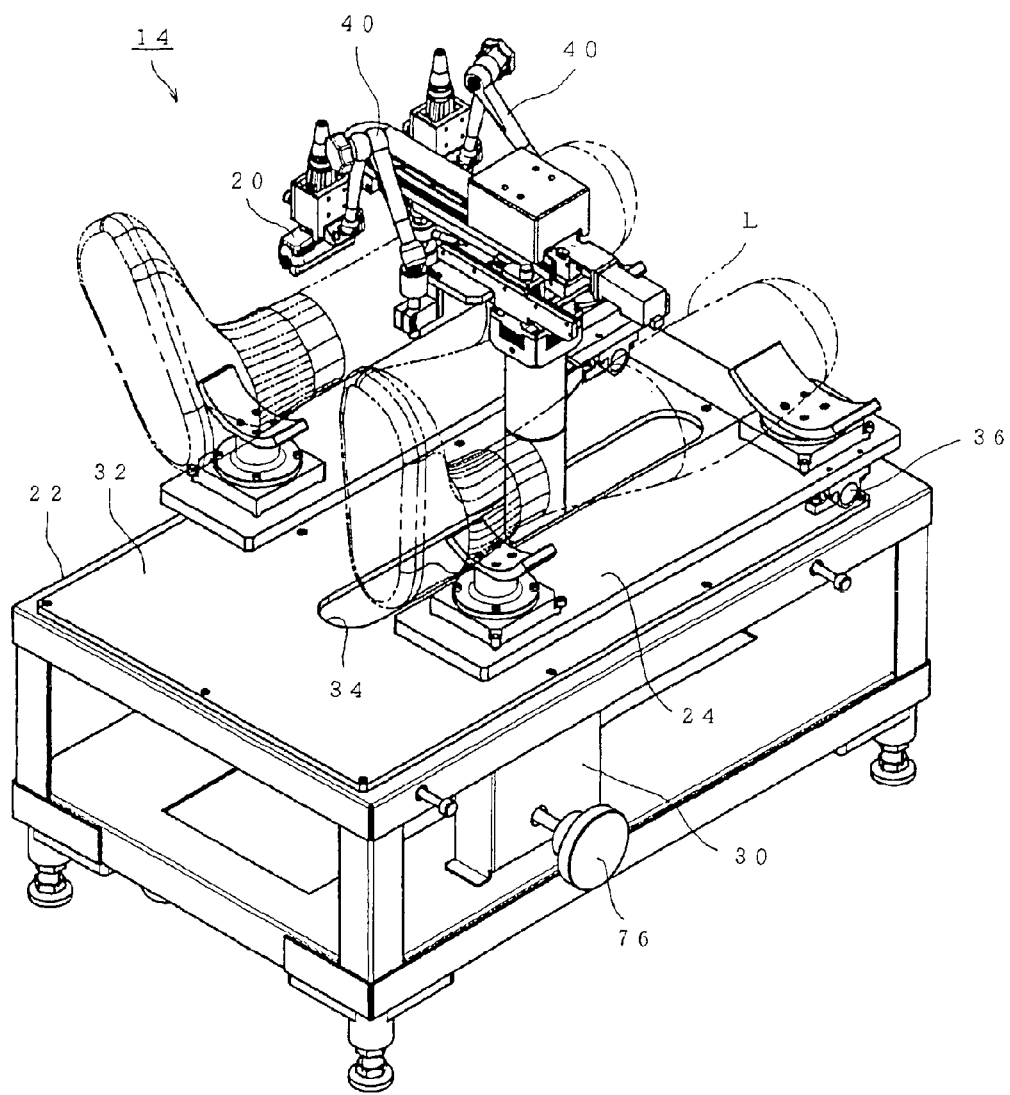
FIG. 3 is a perspective view showing the lower leg support device 14.
Figure 4:
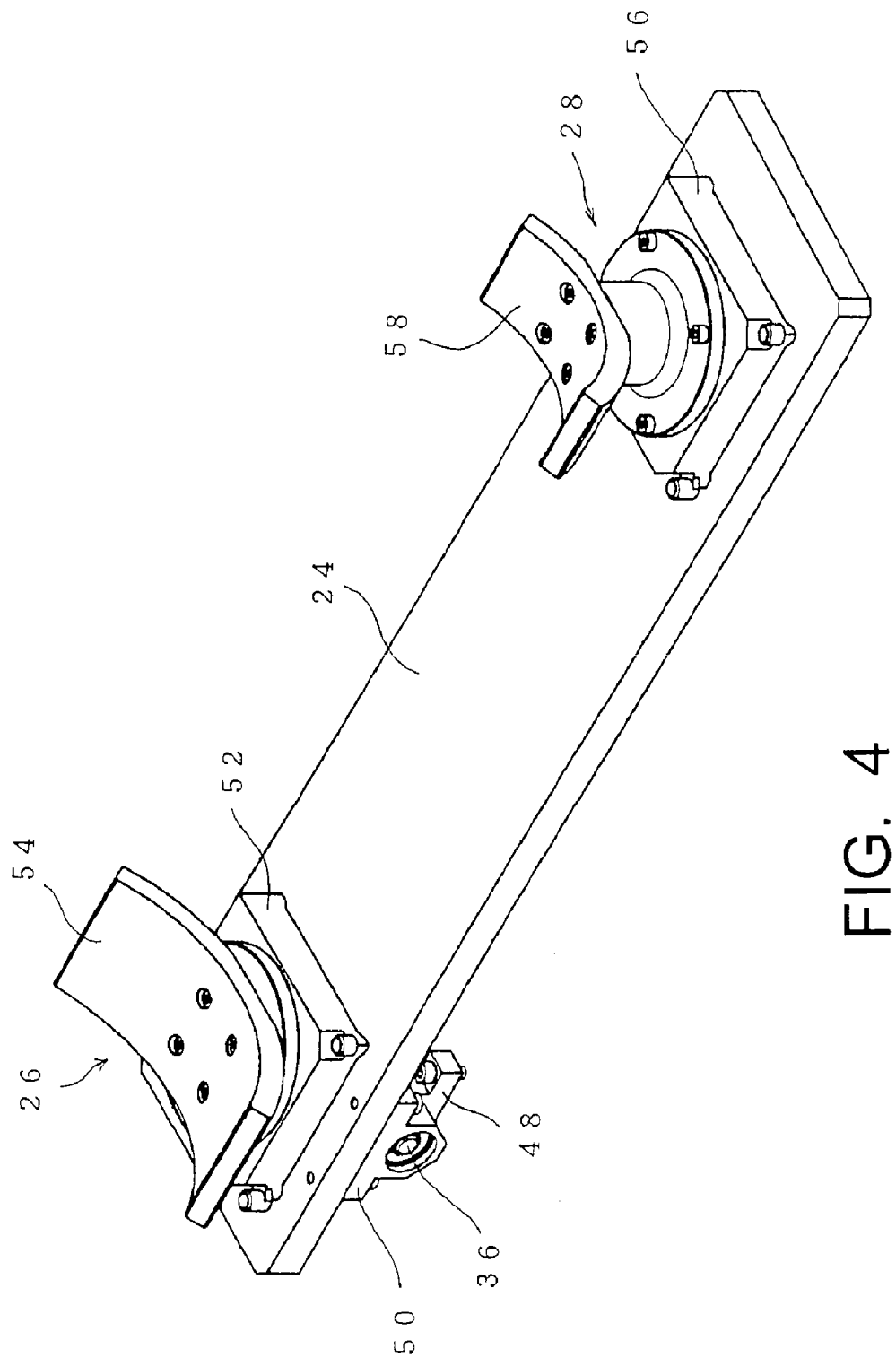
FIG. 4 is a perspective view showing a lower leg support set.
Figure 5:
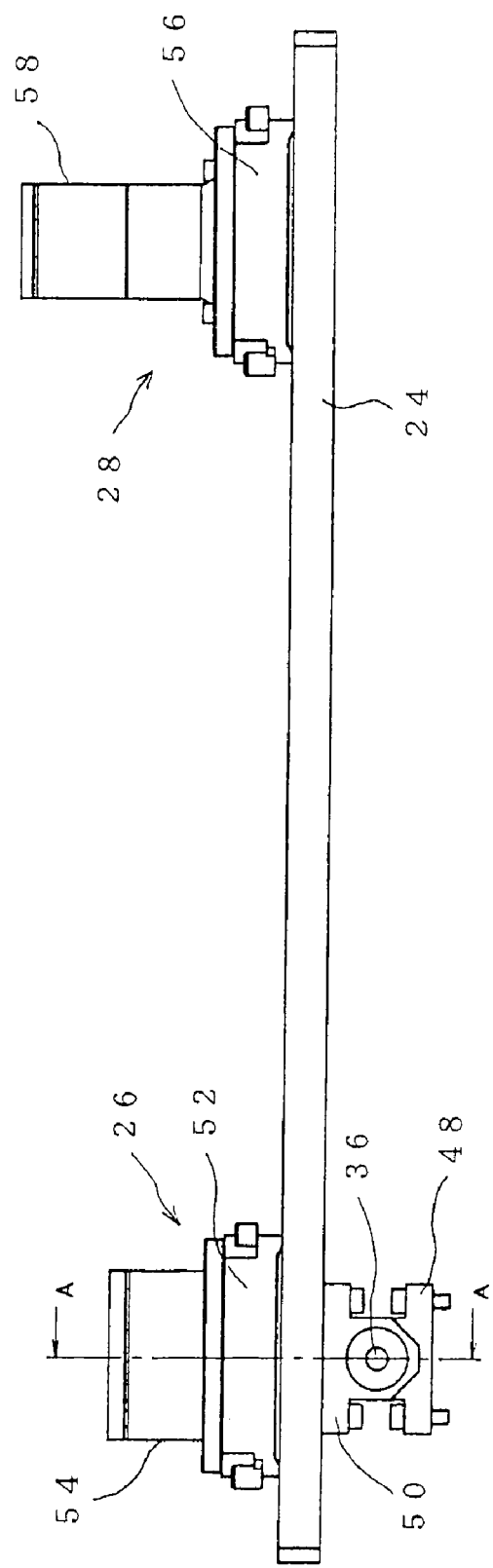
FIG. 5 is a side view of the lower leg support set.
Figure 6:
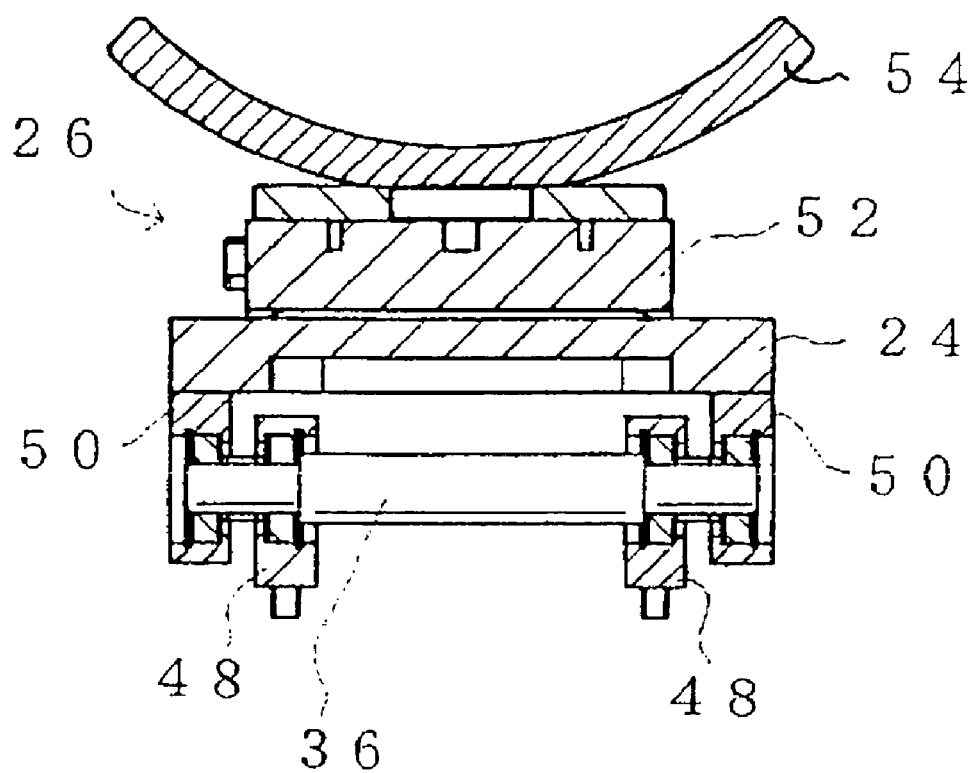
FIG. 6 is a cross-sectional view taken along line A-A shown in FIG. 5.
Figure 7:
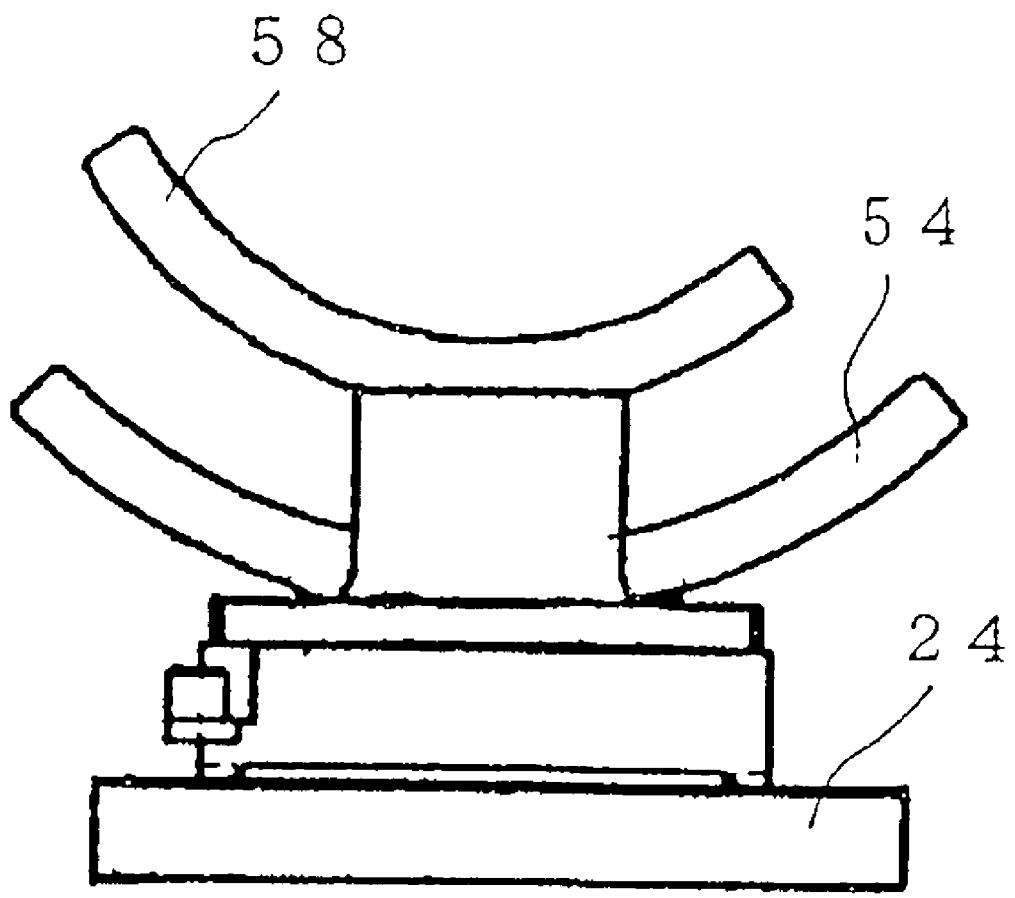
FIG. 7 is a front view of the lower leg support set.
Figure 8:
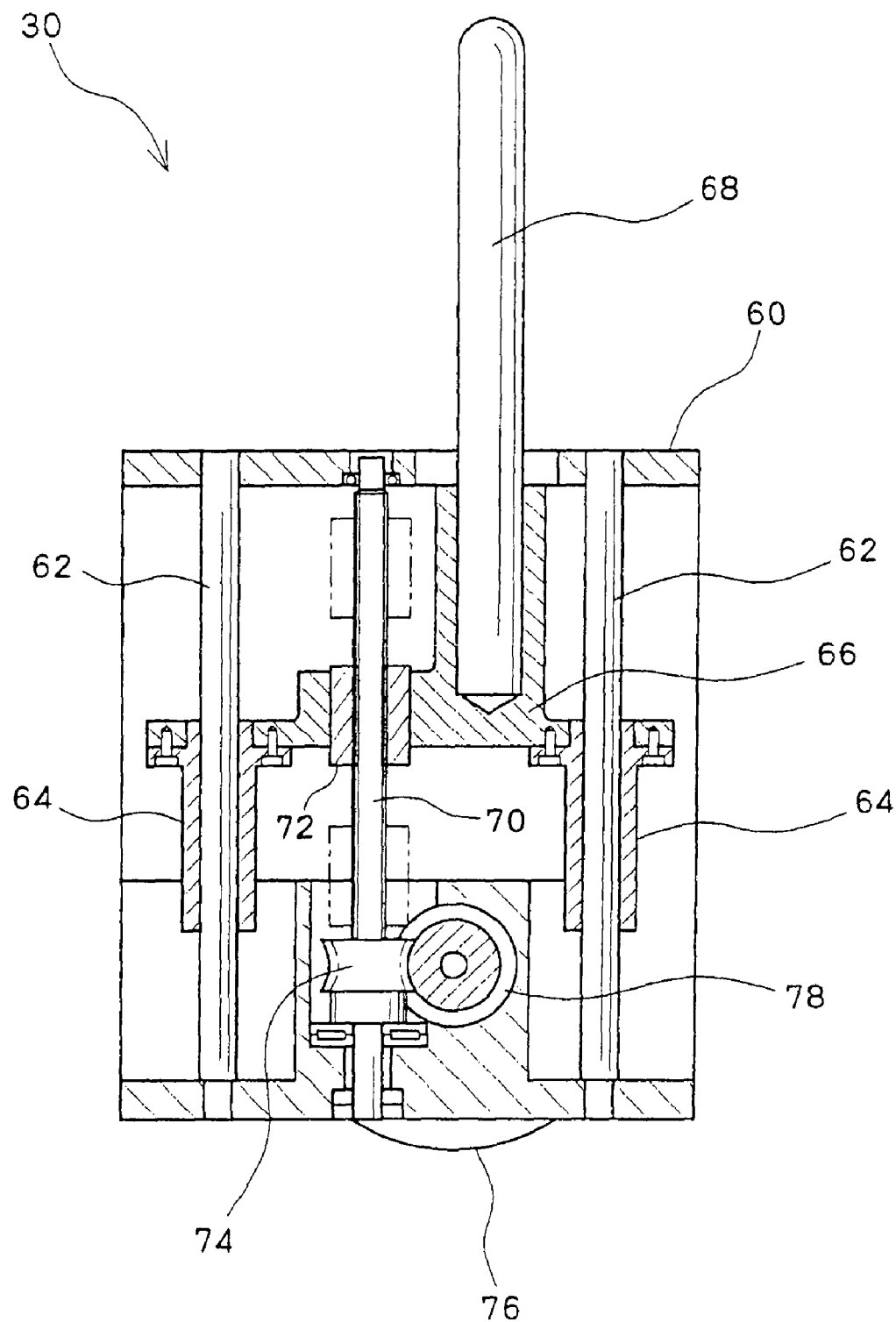
FIG. 8 is a diagram showing an elevating mechanism 30.
Figure 9:
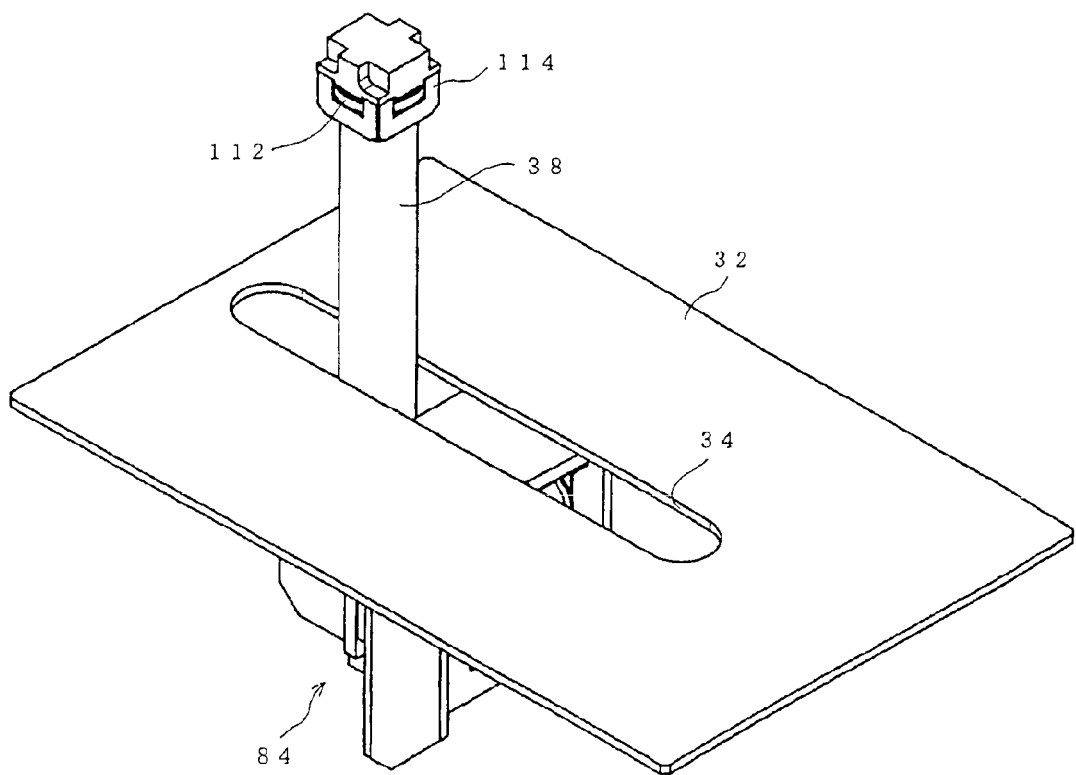
FIG. 9 is a schematic perspective view showing a column and its support structure.
Figure 10:
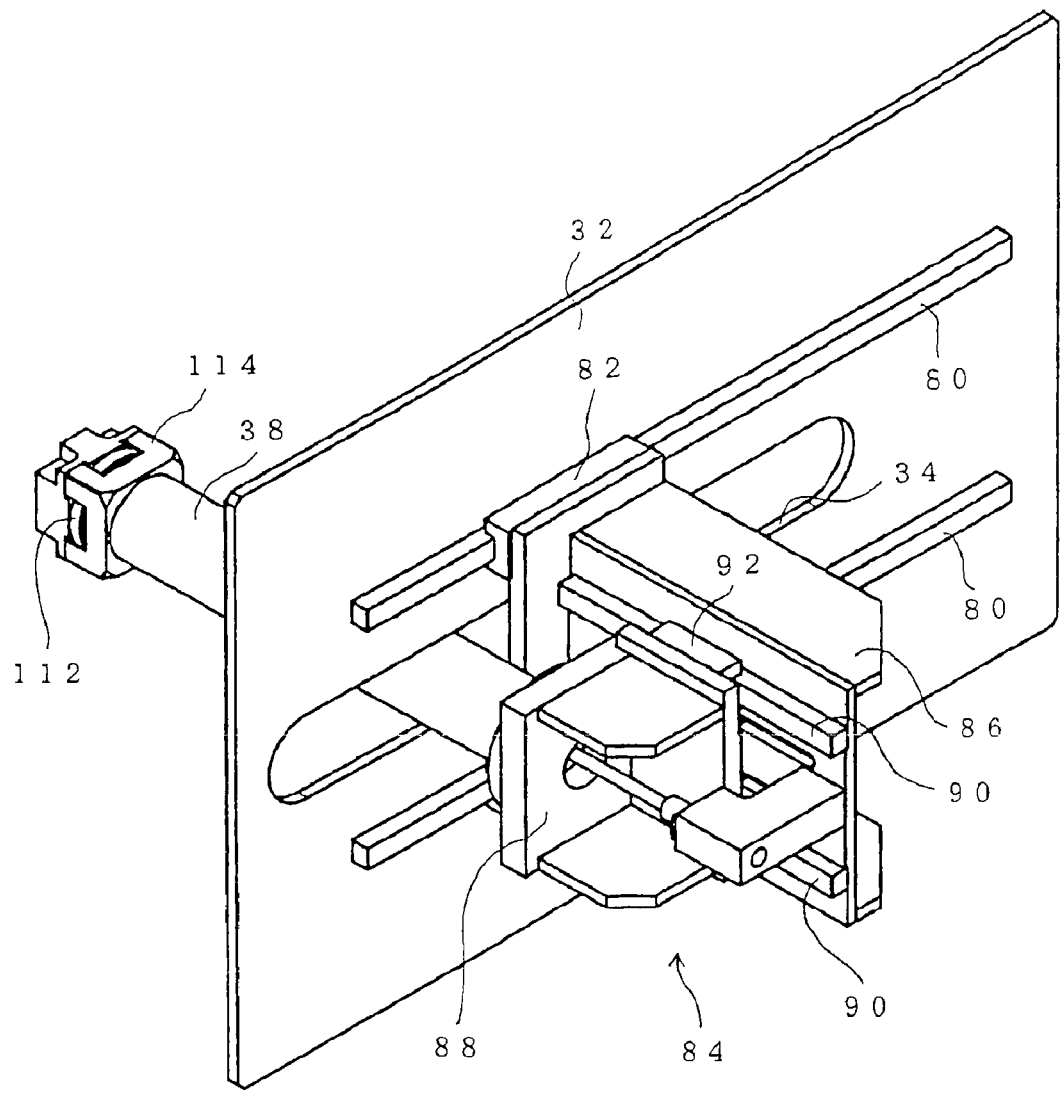
FIG. 10 is a schematic perspective view showing the column and its support structure.
Figure 11:
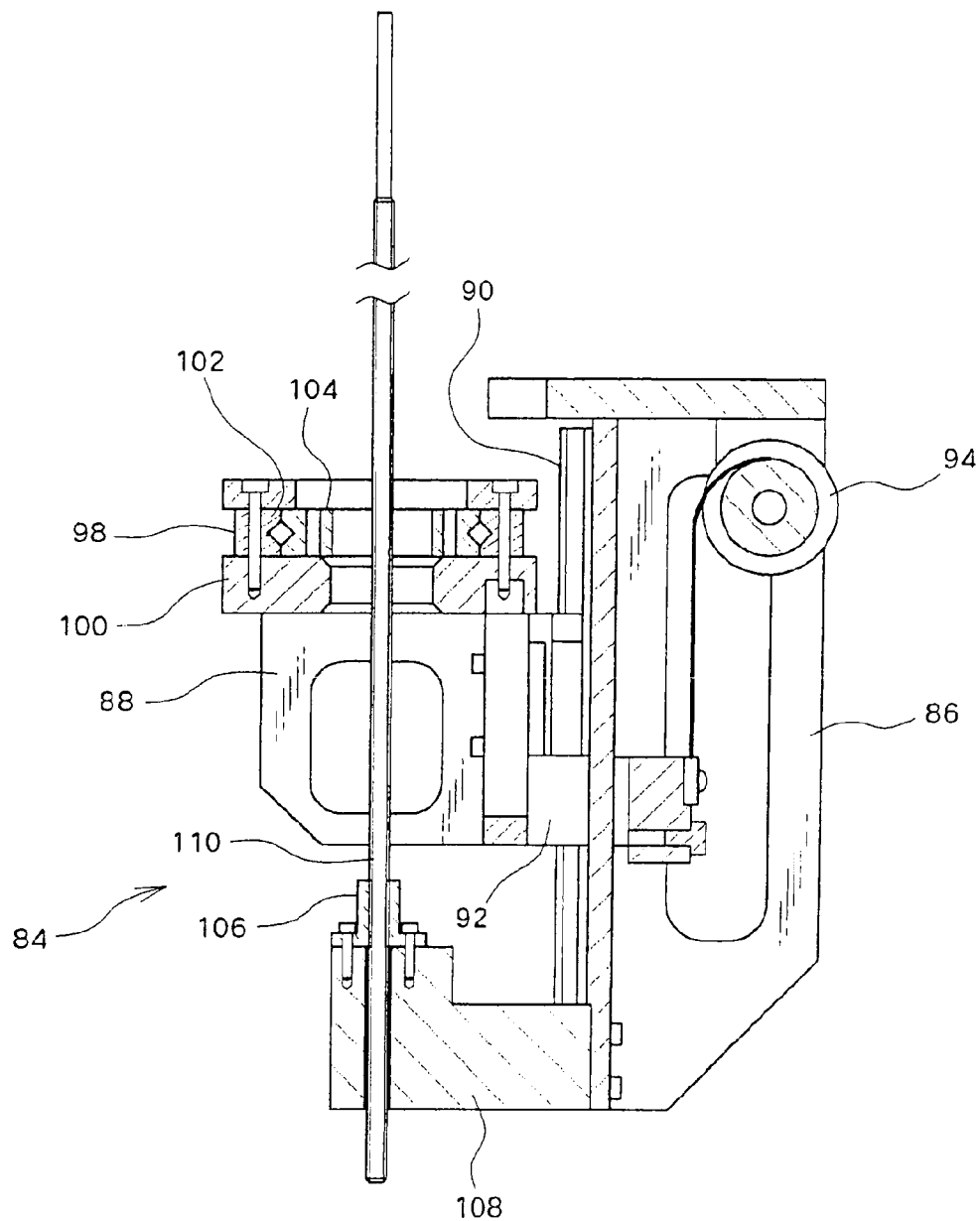
FIG. 11 is a schematic cross-sectional view of the support structure for the column.
Figure 12:
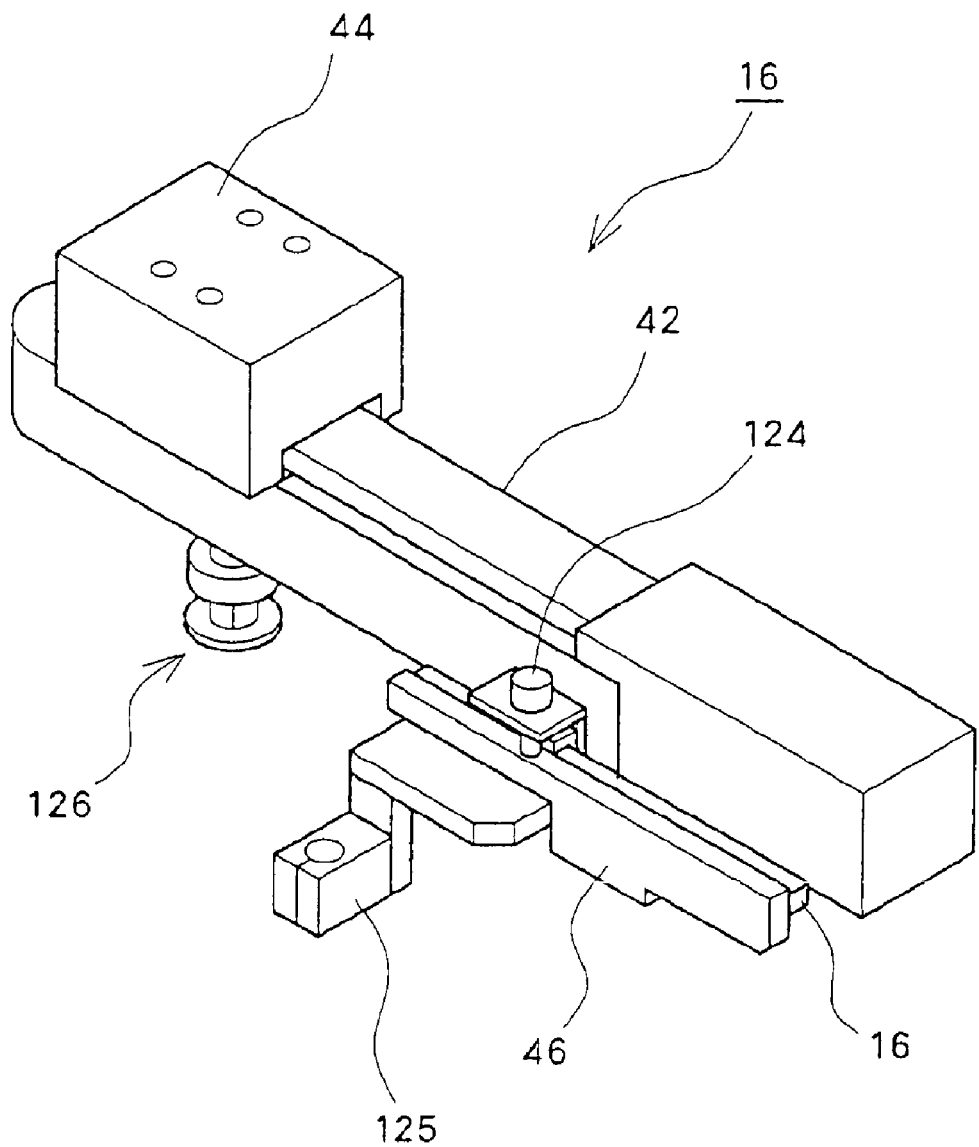
FIG. 12 is a perspective view showing a load applying mechanism 16.
Figure 13:
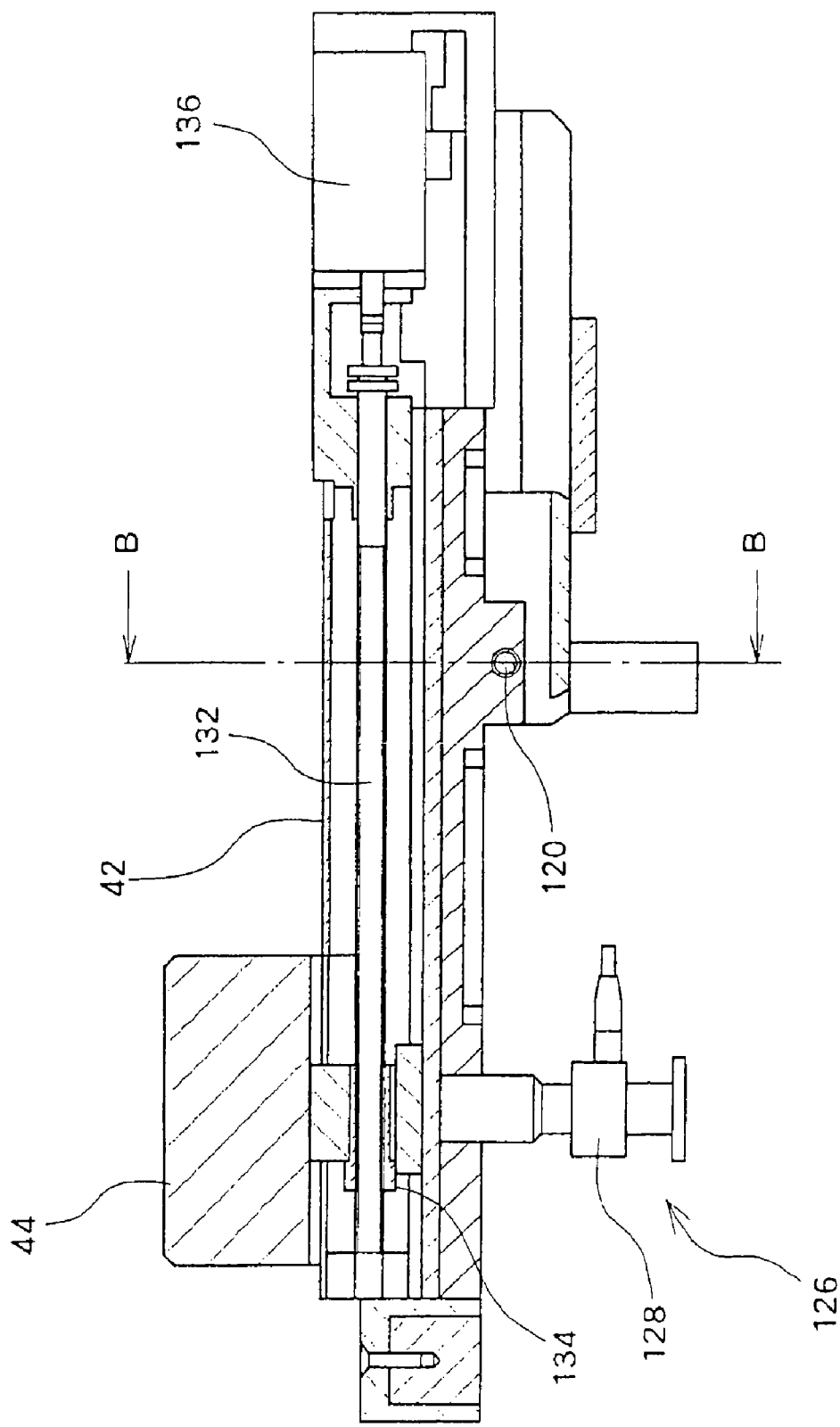
FIG. 13 is a cross-sectional view of the load applying mechanism 16.
Figure 14:
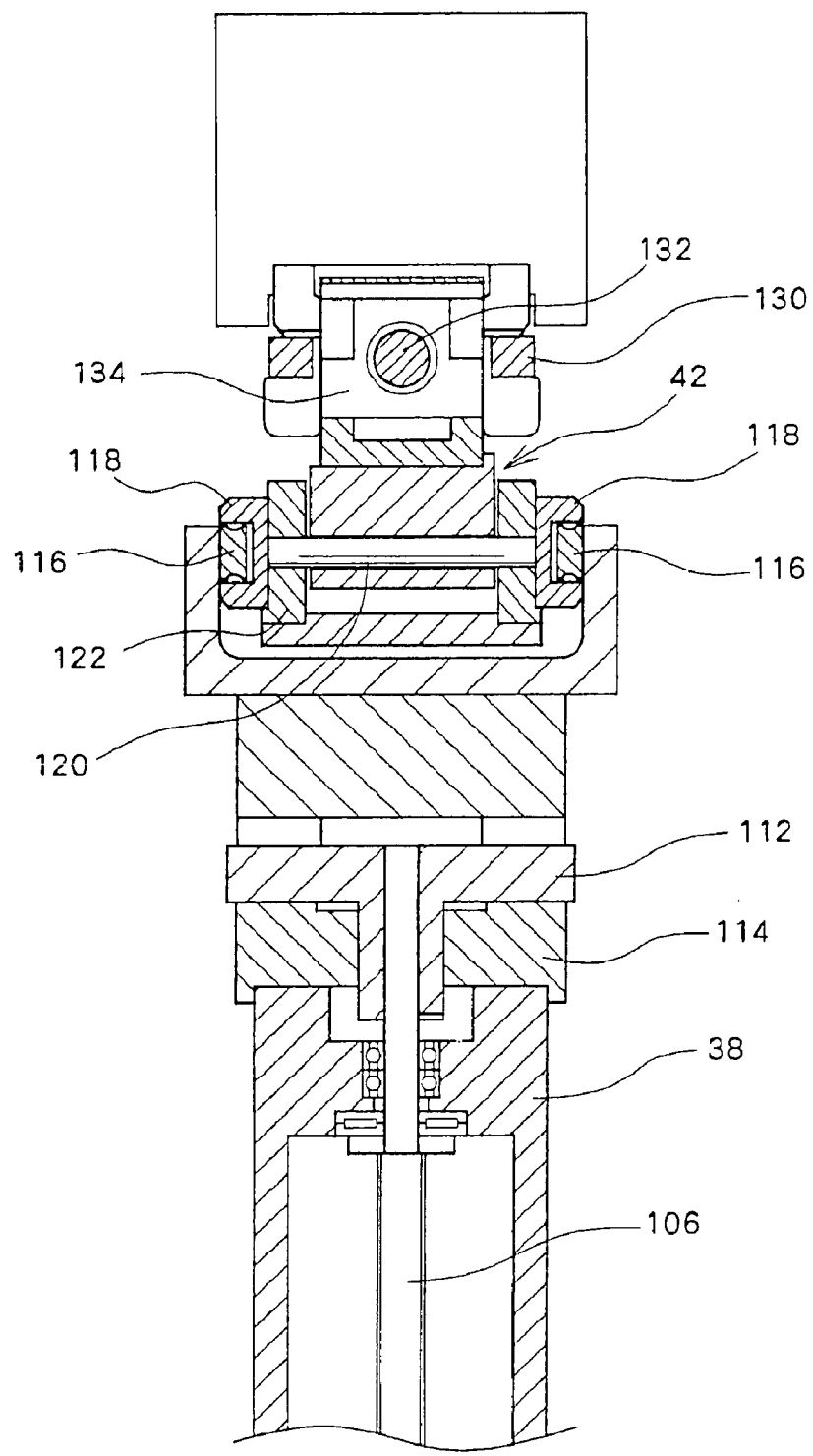
FIG. 14 is a cross-sectional view of the load applying mechanism 16 taken along line B-B shown in FIG. 13.

REFERENCE NUMERALS 10 bone inspection system, 14 lower leg support device, 16 load applying mechanism, 18 ultrasonic diagnosis apparatus, 20 ultrasonic probe, 22 main base, 24 pivoting base, 26 proximal support block, 28 distal support block, 30 elevating mechanism, 36 support axis, 38 column, 42 rocking lever, 44 weight, 46 transverse adjustment guide, 52, 56 magnet base, 84 column support mechanism, 112 adjustment disc, 126 pressing element.

The invention claimed is:

1. A bone inspection system comprising:
a lower leg support device for supporting a lower leg of an examined person;
a load applying mechanism for applying a load to a bone of the supported lower leg,
wherein the load applying mechanism includes a rocking lever and a weight that performs a reciprocating movement along the lever, wherein the load applying mechanism applies periodically-varying load using the reciprocating movement of the weight; and
an ultrasonic unit that transmits and receives ultrasonic waves to and from the lower leg bone and carries out a measurement based on a received ultrasonic signal,
wherein a deformation in the bone caused by the load is measured using the ultrasonic unit,
wherein the lower leg support device comprises:
a main base;
a pivoting base that is pivotably supported with respect to the main base; and
a proximal support member and a distal support member that are provided commonly on the pivoting base and individually support a proximal portion and a distal portion of the lower leg, respectively,
and wherein an axis of pivot of the pivoting base is located at a position corresponding to the proximal portion of the lower leg, and the pivoting action causes the distal portion to be raised and lowered.

2. The bone inspection system according to claim 1, wherein the load applying mechanism is mounted on a column that is supported by a column support mechanism arranged on the main base.

3. The bone inspection system according to claim 1, wherein a mounting position of the distal support member on the pivoting base is changeable.

4. The bone inspection system according to claim 1, wherein mounting positions of the distal support member and the proximal support member on the pivoting base are respectively changeable.

5. The bone inspection system according to claim 1, comprising two lower leg support sets provided commonly on the main base and corresponding to left and right lower legs of the examined person, each lower leg support set including the pivoting base, the proximal support member, and the distal support member, wherein the two lower leg support sets are separately adjustable.

6. The bone inspection system according to claim 5, further comprising a column that is provided between the two lower leg support sets and swingably supports the load applying mechanism, wherein swinging of the load applying mechanism enables the load applying mechanism to selectively face the examined person's left lower leg or right lower leg.

7. The bone inspection system according to claim 6, wherein the ultrasonic unit includes a ultrasonic probe that transmits and receives ultrasonic waves to and from a lower leg bone, wherein the ultrasonic probe is supported on said column, and said swinging enables the ultrasonic probe to selectively face the examined person's left lower leg or right lower leg.

* * * * *